United States Patent
Wild et al.

(10) Patent No.: US 7,239,380 B2
(45) Date of Patent: Jul. 3, 2007

(54) TENSIONING RAIL APPLIED BY INJECTION MOLDING

(75) Inventors: Hans-Peter Wild, Eppelheim/Heidelberg (DE); Eberhard Kraft, Neckarbischofsheim (DE)

(73) Assignee: Deutsche Sisi-Werke GmbH & Co. Betriebs KG, Eppelheim/Heidelberg (DE)

( * ) Notice: Subject to any disclaimer, the term of this patent is extended or adjusted under 35 U.S.C. 154(b) by 218 days.

(21) Appl. No.: 10/863,446

(22) Filed: Jun. 8, 2004

(65) Prior Publication Data

US 2005/0024631 A1 Feb. 3, 2005

(30) Foreign Application Priority Data

Jul. 31, 2003 (EP) .................................. 03017378

(51) Int. Cl.
*G01N 21/00* (2006.01)
(52) U.S. Cl. .................... 356/237.1; 356/239.1
(58) Field of Classification Search ............ None
See application file for complete search history.

(56) References Cited

U.S. PATENT DOCUMENTS

| | | | |
|---|---|---|---|
| 3,650,400 A | | 3/1972 | Warren et al. |
| 5,030,833 A | * | 7/1991 | Nozaka et al. ............ 250/461.1 |
| 5,073,951 A | * | 12/1991 | Hayashi ...................... 382/141 |
| 5,978,093 A | * | 11/1999 | Abrahamson ............... 356/401 |
| 5,979,142 A | | 11/1999 | Kraft et al. |
| 6,069,693 A | * | 5/2000 | Licchesi .................. 356/237.1 |
| 2003/0232158 A1 | * | 12/2003 | Wild et al. ................. 428/34.1 |
| 2004/0202812 A1 | * | 10/2004 | Congard et al. ........... 428/40.1 |

FOREIGN PATENT DOCUMENTS

| CN | 1217994 A | 6/1999 |
|---|---|---|
| DE | 3128280 A1 | 2/1983 |

OTHER PUBLICATIONS

Search Report in EP03017378.
Chinese Office Action dated Apr. 14, 2006 for Chinese Appln. No. 200410050056.4.

* cited by examiner

*Primary Examiner*—Michael P. Stafira
(74) *Attorney, Agent, or Firm*—Stroock & Stroock & Lavan LLP

(57) ABSTRACT

A device for checking (1) whether a first object (2) with an adhesive (4) affixed thereto is glued onto a second object (3) by means of the adhesive (4), including an excitation unit (5) for exciting luminescence of the adhesive (4) and a detection unit (6) for the selective detection of luminescence light of the adhesive (4). Also provided is a device for gluing a first object (2) with an adhesive (4) affixed thereto onto a second object (3) and having an applicator (8) for gluing on the first object (2) and a device for checking (1) Also provided is a method for checking whether a first object (2) with an adhesive (4) affixed thereto is glued onto a second object (3) by means of the adhesive, including excitation of the adhesive (4) to luminescence and the selective detection of the luminescence light generated in the adhesive (4). There is also a method for gluing a first object (2) onto a second object (3) where the first object is glued onto a second object by means of an applicator (8) and where a method for checking is performed.

19 Claims, 2 Drawing Sheets

TENSIONING RAIL APPLIED BY INJECTION MOLDING

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The invention relates to a device and a method for checking whether a first object with an adhesive thereon is glued onto a second object by means of this adhesive. In addition the present invention relates to a device and a method for gluing a first object with an adhesive thereon to a second object.

2. Background of the Invention

In the manufacture of drink packages, such as foil-bags, a drinking straw is often affixed to the drink package. Often the drinking straw is enclosed in a straw-bag on hygienic grounds. The drinking straw or the straw-bag is then affixed to the drink package with adhesive, the adhesive possibly being affixed to the drinking straw or the straw-bag in advance.

Since errors can occur when affixing the drinking straw to the drink package, it is necessary in a further step to check whether a drinking straw actually has been affixed to a drink package.

SUMMARY OF THE INVENTION

It is therefore the object of the present invention to provide a device and a method for checking whether a first object has been glued onto a second object which perform the check reliably and which function as reliably as possible.

In addition it is an object of the present invention to provide a device and a method for gluing a first object to a second object with which the gluing is performed reliably.

In the case of the device an excitation unit is provided which can excite the emission of luminescence light by the adhesive. This excitation unit can e.g. be an illumination unit with which the adhesive can be illuminated. Luminescence light, which originates in the adhesive, can be detected with a detection unit for the selective detection of the luminescence light. The detector should, as far as possible, selectively detect only the luminescence light but not the excitation (e.g. the light of the illumination unit). This can e.g. be achieved by providing the detection device with an appropriate spectral filter which substantially screens out (e.g. absorbs or reflects) the light of the illuminating unit while permitting the luminescence light of the adhesive to pass through. Every such frequency- or wavelength-sensitive detection or also selection of the luminescence light in some other way is possible according to the present invention. The preferred form of luminescence is fluorescence, which, other than in the case of phosphorescence, results immediately and not with a time delay.

BRIEF SUMMARY OF THE INVENTION

The device preferably has a unit for blacking out the first and the second object so that detection is as little affected as possible by background light.

However, it is also possible to design the detection unit and/or the excitation unit such that there is no chance of background light causing interference. This can e.g. be effected by supplying the detector signal to a lock-in amplifier, the reference signal for the lock-in amplifier being obtained by a modulation of the excitation (e.g. of the illumination light).

Another possibility is that the excitation unit (illumination unit) transmits only one excitation pulse or a plurality thereof (light pulses) and the detection unit accordingly detects only one short detection pulse or a plurality thereof, thus indicating that what is involved is luminescence light and not background light.

If the intensity of the luminescence light is intrinsically sufficiently strong compared to the background light, it is also possible to dispense with blacking out or some other discrimination means.

The device for gluing a first object with an adhesive thereon to a second object can e.g. be effected with an appropriately designed applicator, which glues a first object successively or simultaneously onto a single second object or a plurality thereof. The applicator may also comprise a plurality of applicator units which e.g. in turn provide the succession of second objects with the first objects.

The device is provided with a checking device downstream of the applicator or an applicator unit.

In the method for checking whether a first object with an adhesive thereon is glued onto a second object by means of the adhesive, the adhesive is excited, i.e. is e.g. illuminated with light, and the luminescence light excited by the adhesive is then selectively detected.

Here it is advantageous if the adhesive is easily accessible optically, which is rendered possible e.g. by a first object which is at least partially transparent.

In the case of drinking straws sealed into foil-bags or straw-bags, it suffices if the adhesive is also visible at the side of the drinking straw if the straw itself is not sufficiently transparent.

The adhesive is preferably provided with a luminescence dye of a suitable concentration. Concentrations in the range from hundredths of a per cent up to one, two, five or more per cent are advantageous here. A concentration in the range between 0.1 and 1.0 per cent is particularly advantageous. This is always dependent on the dye which is actually used and its luminescent power, however, since different dyes luminesce to different degrees. Different luminescence dyes absorb and generate light at different wavelengths. Advantageous is a luminescence dye which absorbs light in the ultraviolet spectral region and emits in the visible, preferably in the blue, spectral region.

The illumination units and the detection units must be suitably matched (e.g. as regards light intensity or wavelength) to the luminescence dye which is used.

In the method for gluing on a first object, therefore, an adhesive with appropriate luminescence is used and after the first object has been glued onto the second object a method for checking whether a first object has been glued onto a second object is performed.

BRIEF DESCRIPTION OF THE SEVERAL VIEWS OF THE DRAWINGS

An embodiment of the device and of the methods is described making reference to the enclosed drawings, where.

DETAILED DESCRIPTION OF THE INVENTION

Figure 1:
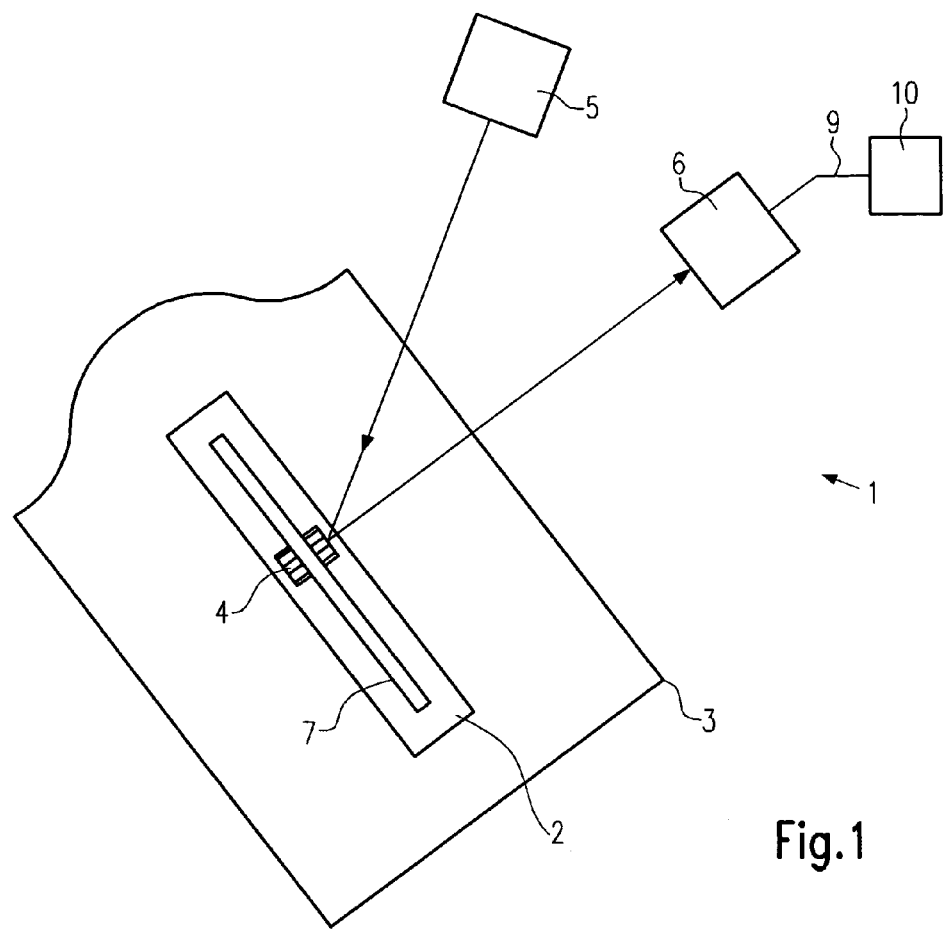
FIG. 1 shows a schematic representation of a device for checking whether a first object is glued onto a second object.

In FIG. 1 the foil-bag 3 is shown in a supine position. A straw-bag 2 is glued onto the foil-bag 3 with adhesive 4. The straw-bag 2 encloses a drinking straw 7. The straw-bag 2 is made of a transparent plastic.

An illumination unit 5 is so designed that it can illuminate the adhesive 4 with light. The adhesive 4 emits luminescence light when it is illuminated. This luminescence light can be detected with a suitably arranged detection unit 6. The detection unit 6 is connected to an evaluation unit 10 via a signal lead 9. The evaluation unit 10 decides, on the basis of the detection signal of the detection unit 6, whether adhesive 4 is present or not. Since the straw-bag 2 is provided with adhesive 4 before the straw-bag 2 is glued onto the foil-bag 3, the presence of the straw-bag 2 can be inferred from the presence of the adhesive 4.

Figure 3:
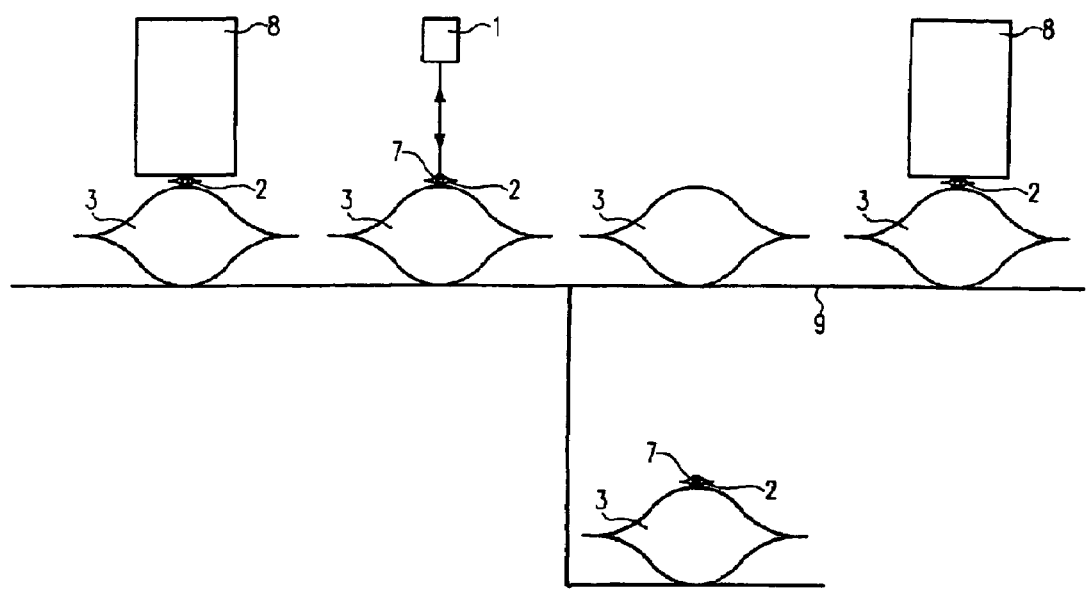

FIG. 3 is a schematic representation of a device in accordance with an embodiment of the invention.

DETAILED DESCRIPTION OF THE INVENTION

In the method a foil-bag 3 is brought into the region of the device for checking 1. This can be achieved e.g. with a conveyor belt or some other conveyor. The illumination unit 5 illuminates the adhesive 4 which, should its intrinsic luminescence be insufficient, is provided with a suitable luminescence dye. The luminescence light thus generated is detected by the detection unit 6. The detection signal is forwarded to an evaluation unit 10 via a signal lead 9. The evaluation unit 10 now controls the rejection of the foil-bag 3, recognized as faulty if no adhesive 4 was detected on it. The excluded foil-bag 3 can e.g. be submitted again to the application of straw-bags.

It is also possible for the evaluation unit 10 to induce a post-circuited applicator to affix a straw-bag 2 with a drinking straw 7 therein.

It will be advantageous to ascertain in some suitable way whether a foil-bag 3 is present in the region of the checking device 1 or not. Only if a foil-bag 3 is present can the presence or absence of the adhesive 4 be detected. Detecting whether or not a foil-bag is present can be accomplished e.g. with a light barrier or a proximity sensor operating optically or acoustically. A sensor for detecting metal (e.g. aluminium) such as is used in foil-bags or drink packages is also suitable here.

Figure 2:
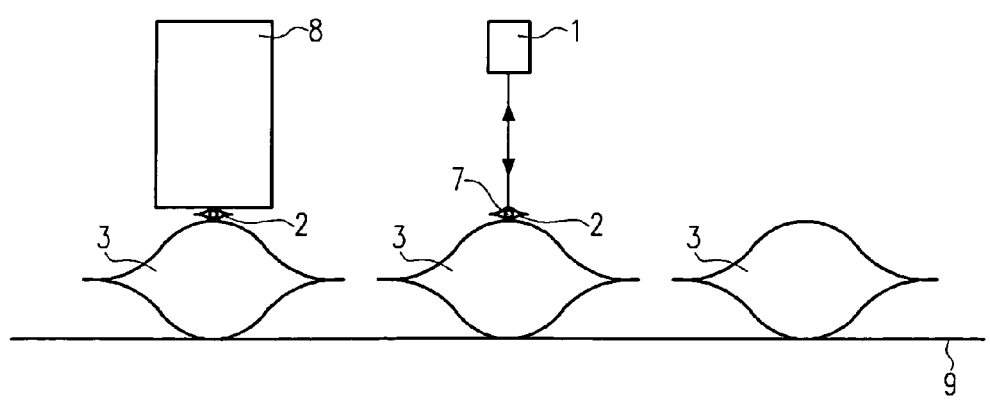
FIG. 2 shows a representation of a device for gluing a first object onto a second object.

A device for gluing a straw-bag 2 to a foil-bag 3 is shown in FIG. 2. An applicator 8 serves to glue a straw-bag 2 to the foil-bag 3. Here the straw-bag 2 has adhesive 4 affixed to it via which the straw-bag 2 is stuck to the foil-bag 3.

While only one device 8 is shown as applicator in FIG. 2, the applicator 8 may itself comprise a plurality of application units, which can e.g. affix the straw-bags 2 to the foil-bags 3 in turn.

FIG. 2 shows a conveyor belt 9 with which the foil-bags 3 can be conveyed from the applicator 8 to the checking device 1.

The device 1 is here located downstream from the applicator 8 and serves to check whether a straw-bag 2 has been glued to the foil-bag 3.

Downstream from the checking device 1 a rejection unit, which is not shown in FIG. 2, is provided which rejects foil-bags 3 which do not have a straw-bag 2. Instead, an additional applicator 8 can be provided which affixes the missing straw-bag 2.

The rejection unit or the additional applicator 8 can also be located, at the device 1 so that rejection or the affixing of a first object 2 can occur immediately after detection.

In the method for gluing, a foil-bag 3 is conveyed to the applicator 8 on the conveyor belt 9 and is there provided with a straw-bag 2. The foil-bag 3 is then conveyed to the checking device 1 with the conveyor 9. Here, as has been explained with reference to FIG. 1, it is checked whether adhesive 4, and thus the straw-bag 2, is present. The foil-bag 3 is then conveyed further on the conveyor 9 to be either rejected or to have a straw-bag 2 affixed to it subsequently if a straw-bag 2 is missing. Rejection or affixation can also take place immediately after checking without previously transporting the foil-bag much further.

The invention claimed is:

1. A device for checking for the presence of an adhesive on a drink package to confirm whether a straw bag is affixed to the drink package at a predetermined position on the drink package, the device comprising an illumination unit constructed and positioned to illuminate the adhesive at the predetermined position and a detection unit constructed and positioned to detect the presence or absence of luminescence light that illuminates the adhesive at the predetermined position.

2. A device according to claim 1, wherein the illumination unit is constructed and arranged to excite the adhesive.

3. A device according to claim 1, wherein the detection unit is constructed and arranged to detect light in the visible spectral region.

4. A device according to claim 1, wherein the detection unit generates a detection signal, the device further comprising an evaluation unit constructed and arranged to evaluate the detection signal of the detection unit.

5. A device according to claim 2, wherein the illumination unit is constructed and arranged to illuminate the adhesive with UV light.

6. A device according to claim 3, wherein the detection unit is constructed and arranged to detect luminescence light in the blue spectral region of the visible spectral region.

7. A device according to claim 1, wherein the straw-bag is at least partly transparent.

8. A device according to claim 1, wherein the drink package is a foil-bag.

9. A method for checking for the presence of an adhesive on a drink package to confirm whether a straw bag is affixed to the drink package at a predetermined position, the method comprising illuminating the adhesive at the predetermined position, and selectively detecting the presence of absence of a luminescence light illuminating the adhesive at the predetermined position.

10. A method according to claim 9, wherein the illuminating the adhesive comprises exciting the adhesive with a light.

11. A method according to claim 9, wherein the detection occurs in the visible spectral region.

12. A device according to claim 9, wherein the adhesive contains a luminescence dye.

13. A method according to claim 10, wherein the light is UV light.

14. A method according to claim 11, wherein the detection occurs in the blue spectral region.

15. A method according to claim 8, wherein the drink package is a foil-bag.

16. A device for affixing and confirming that a straw-bag having an adhesive is affixed to is affixed to a drink package at a predetermined position, the device comprising an applicator for affixing the straw-bag onto the drink package at the predetermined position, an illumination unit constructed and positioned to illuminate the adhesive at the predetermined position, and a detection unit for the selective detection of a presence or absence of luminescence light illuminating the adhesive at the predetermined position.

17. A device according to claim 16, further comprising one of a rejection unit, constructed and positioned to reject a drink package without a straw bag affixed thereto, and an additional applicator, constructed and positioned to affix another straw-bag to the drink package, the rejection unit and the additional applicator being at or downstream from the device.

18. A method for affixing and confirming that a straw-bag is affixed onto a drink package at a predetermined position, the method comprising affixing a straw-bag onto a drink package at the predetermined position by an adhesive; illuminating the adhesive at the predetermined position until the adhesive generates a luminescence light; and selectively detecting the luminescence light generated in the adhesive at the predetermined position.

19. A method according to claim 18, further comprising rejecting the drink package and affixing another straw-bag to the drink package.

* * * * *